(12) United States Patent
Sternick

(10) Patent No.: US 10,174,277 B1
(45) Date of Patent: Jan. 8, 2019

(54) MEDIA TRAY SYSTEM

(71) Applicant: John L. Sternick, Brandon, SD (US)

(72) Inventor: John L. Sternick, Brandon, SD (US)

( * ) Notice: Subject to any disclaimer, the term of this patent is extended or adjusted under 35 U.S.C. 154(b) by 51 days.

(21) Appl. No.: 15/398,265

(22) Filed: Jan. 4, 2017

(51) Int. Cl.
| | |
|---|---|
| *C12M 1/00* | (2006.01) |
| *C12M 1/22* | (2006.01) |
| *C12M 3/00* | (2006.01) |
| *B65D 43/16* | (2006.01) |
| *B65D 43/24* | (2006.01) |

(52) U.S. Cl.
CPC .......... *C12M 23/10* (2013.01); *B65D 43/163* (2013.01); *B65D 43/24* (2013.01); *C12M 23/38* (2013.01); *C12M 23/48* (2013.01)

(58) Field of Classification Search
CPC ....... C12M 23/12; C12M 23/32; C12M 23/48
See application file for complete search history.

(56) References Cited

U.S. PATENT DOCUMENTS

| | | | |
|---|---|---|---|
| 3,532,604 A | | 10/1970 | Bloch |
| 4,072,577 A | | 2/1978 | Hirshaut |
| 4,495,289 A | * | 1/1985 | Lyman et al. ......... C12M 23/38 |
| | | | 422/504 |
| 4,847,128 A | | 7/1989 | Dorn |
| 5,520,302 A | | 5/1996 | Anderson |
| 5,812,312 A | * | 9/1998 | Lorincz ................... G01N 1/30 |
| | | | 359/396 |
| 2005/0003525 A1 | | 1/2005 | Hsu |
| 2011/0003376 A1 | | 1/2011 | Gulzow |
| 2011/0189782 A1 | | 8/2011 | Testa |
| 2013/0095009 A1 | | 4/2013 | Huet |

FOREIGN PATENT DOCUMENTS

| | | |
|---|---|---|
| EP | 0119984 | 2/1984 |
| EP | 0171174 | 2/1986 |
| EP | 1035201 | 9/2000 |
| FR | 2795089 | 12/2000 |

* cited by examiner

*Primary Examiner* — Gautam Prakash
(74) *Attorney, Agent, or Firm* — Jeffrey A. Proehl; Woods, Fuller, Shultz & Smith, PC

(57) ABSTRACT

A media tray system may include a tray having a base wall and a perimeter wall extending upwardly from the base wall and having an upper edge. The system may also include a cover having a top wall and a side wall extending downwardly from the top wall to extend about the perimeter wall of the tray when the cover is in a closed condition with respect to the tray, with the side wall having a lower edge. The system may further include a cover support structure located at the first end of the tray and the first end of the first end of the cover. The cover support structure may be configured to support the cover in an access condition permitting access to the tray interior of the tray through a gap formed between an upper edge of the tray and the lower edge of the cover.

23 Claims, 14 Drawing Sheets

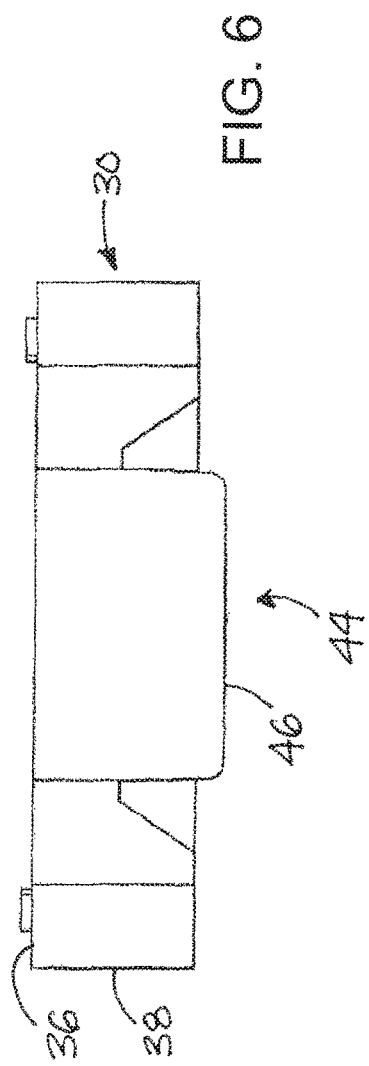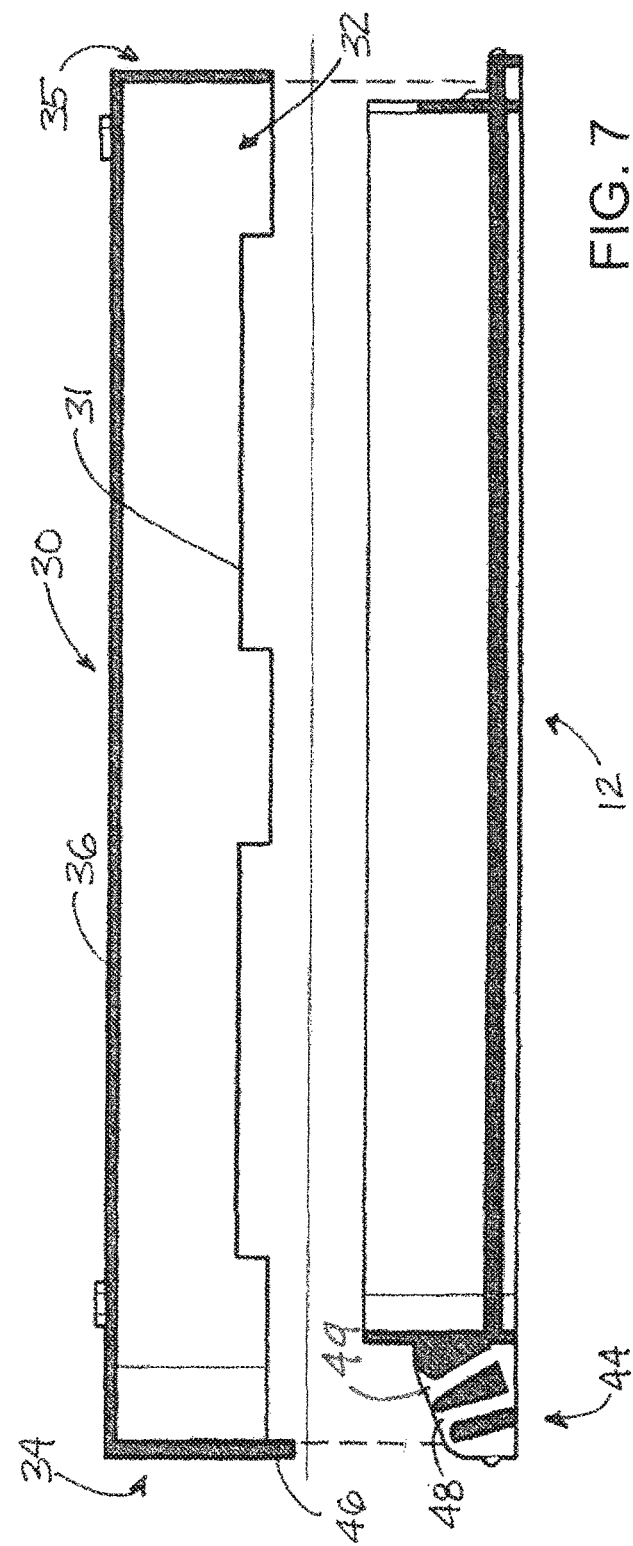

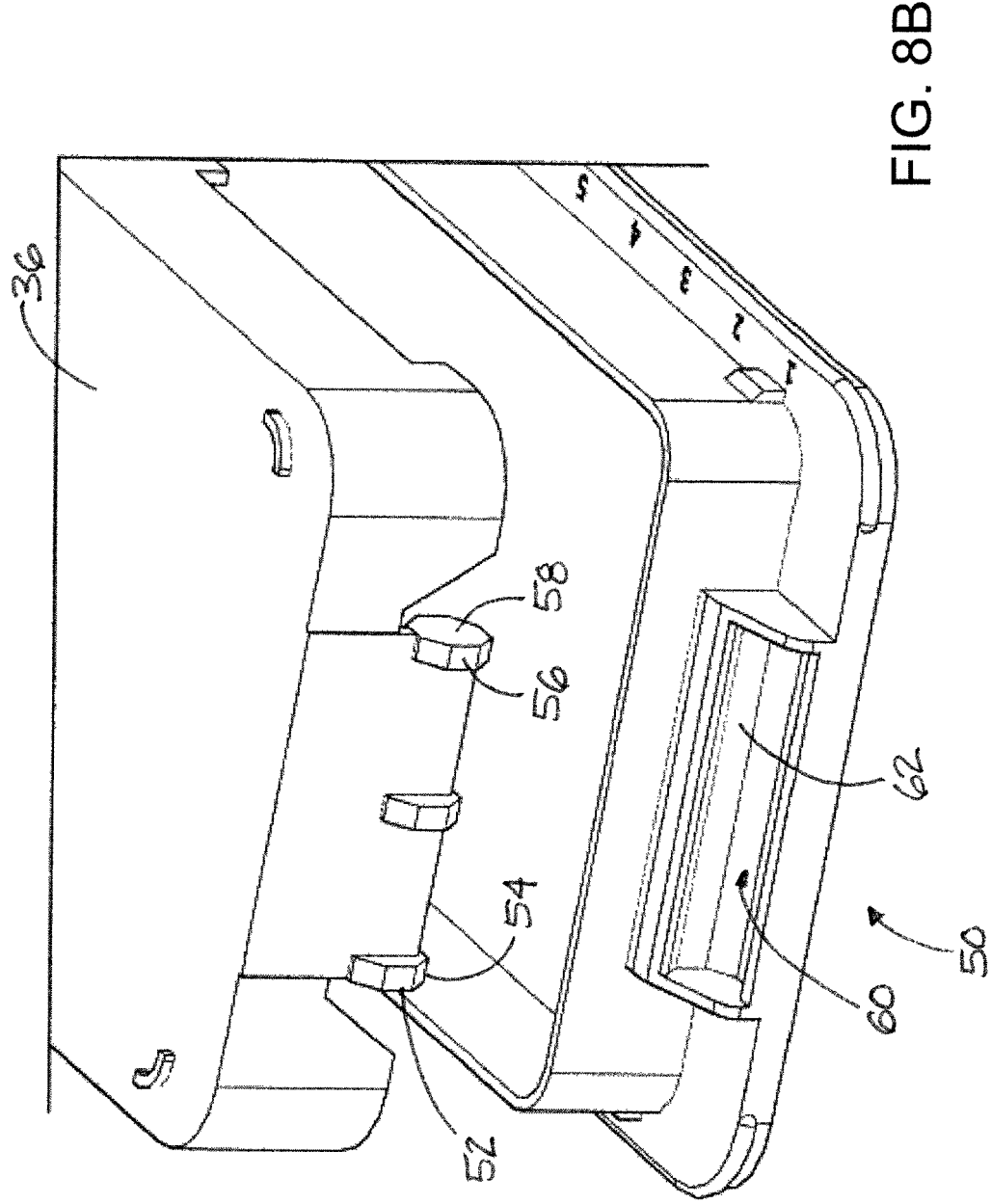

US 10,174,277 B1

MEDIA TRAY SYSTEM

BACKGROUND

Field

The present disclosure relates to laboratory tools and more particularly pertains to a new media tray system for facilitating the manipulation of samples in a protective environment.

SUMMARY

The present disclosure relates to a media tray system which may comprise a tray having a base wall and a perimeter wall extending upwardly from the base wall to define a tray interior. The perimeter wall has an upper edge opposite of the base wall which may define at least a portion of an upper opening of the tray. The system may also include a cover having a top wall and a side wall extending downwardly from the top wall to extend about the perimeter wall of the tray when the cover is in a closed condition with respect to the tray, and the side wall has a lower edge. The system may also include a cover support structure located at the first end of the tray and the first end of the first end of the cover. The cover support structure may be configured to support the cover in an access condition permitting access to the tray interior of the tray through a gap formed between an upper edge of the tray and the lower edge of the cover.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components, or the particulars of the steps, set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein:

FIG. 6 is a schematic end view of the cover of the system, according to an illustrative embodiment.

FIG. 7 is a schematic sectional view of the cover and tray of the system shown in an exploded relationship, according to an illustrative embodiment.

FIG. 8B is a schematic perspective end view of the cover and tray of the system embodiment shown in FIG. 8A, according to an illustrative embodiment.

DETAILED DESCRIPTION

Figure 1A:
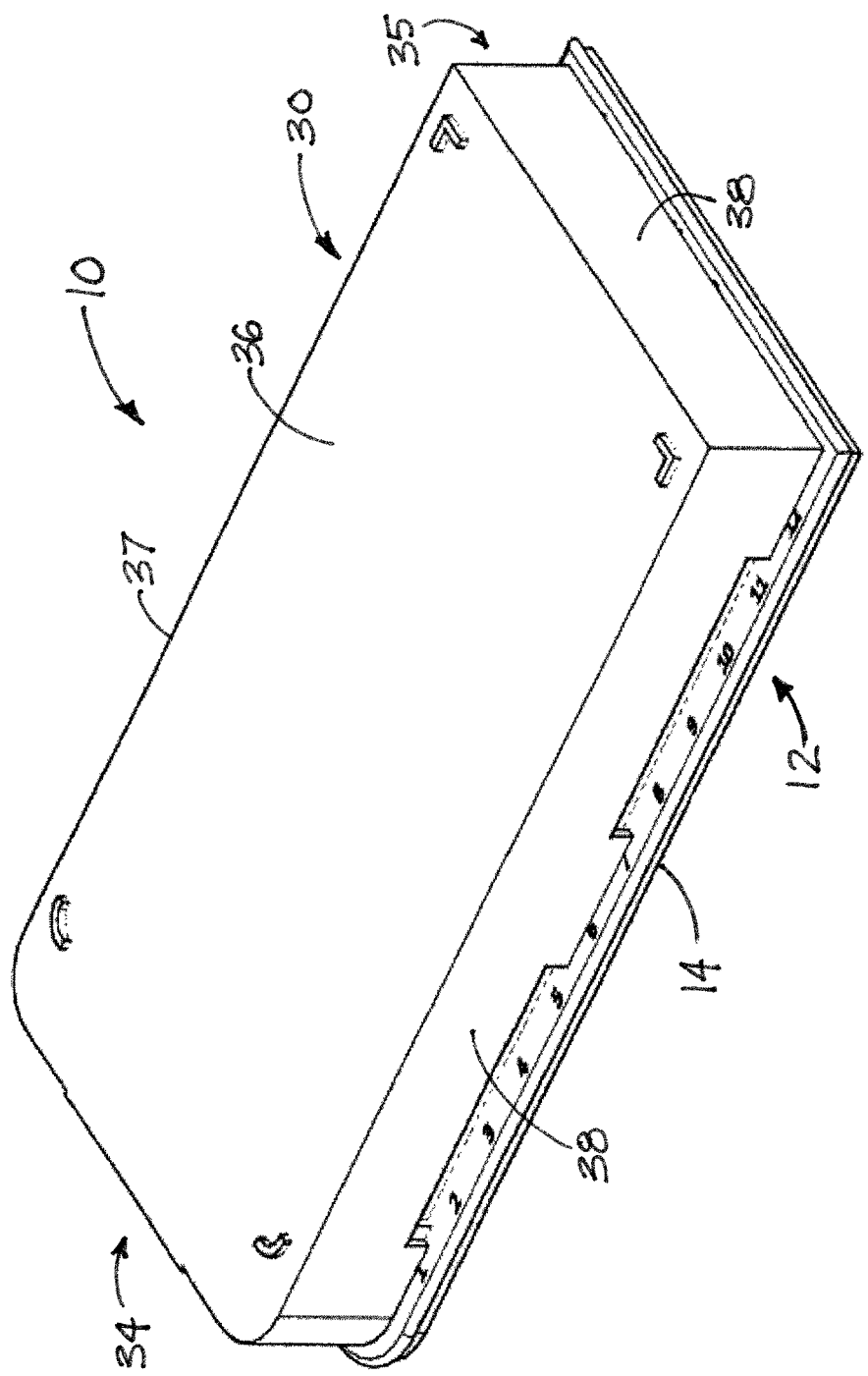
FIG. 1A is a schematic perspective view of a new media tray system in a closed condition, according to the present disclosure.
Figure 1B:
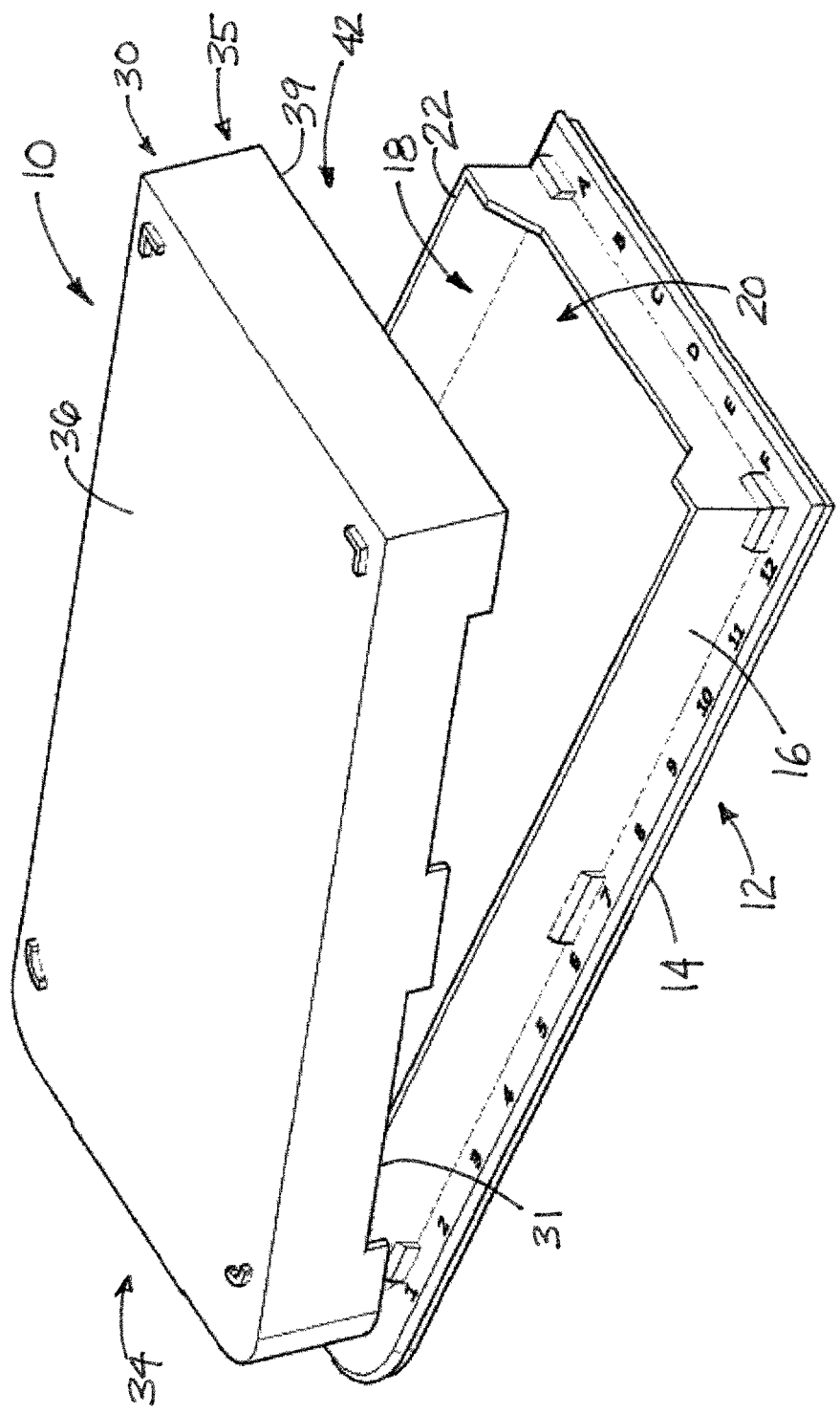
FIG. 1B is a schematic perspective view of the media tray system in one illustrative access condition, according to an illustrative embodiment.
Figure 1C:
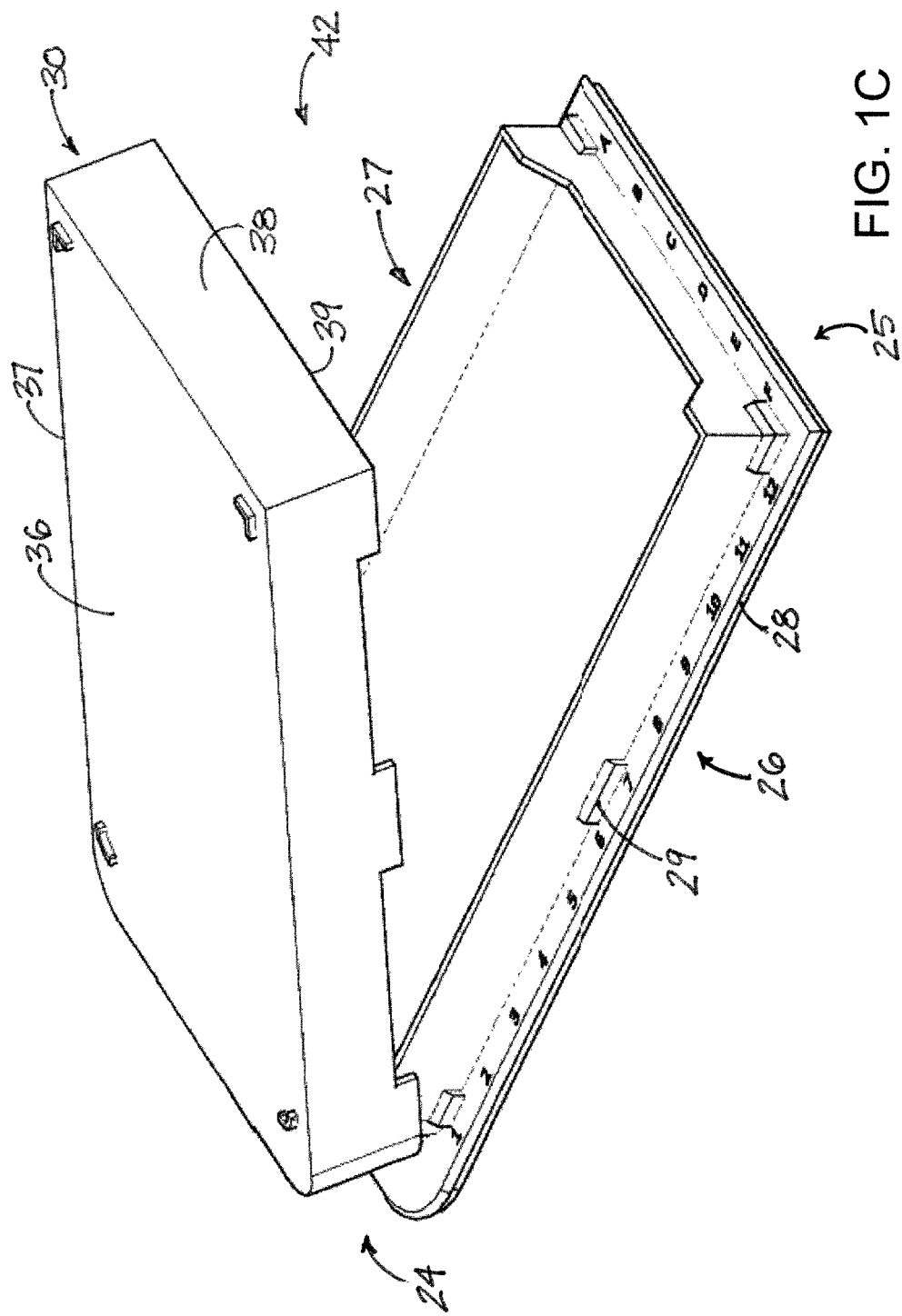
FIG. 1C is a schematic perspective view of the media tray system in another illustrative access condition, according to an illustrative embodiment.
Figure 2:
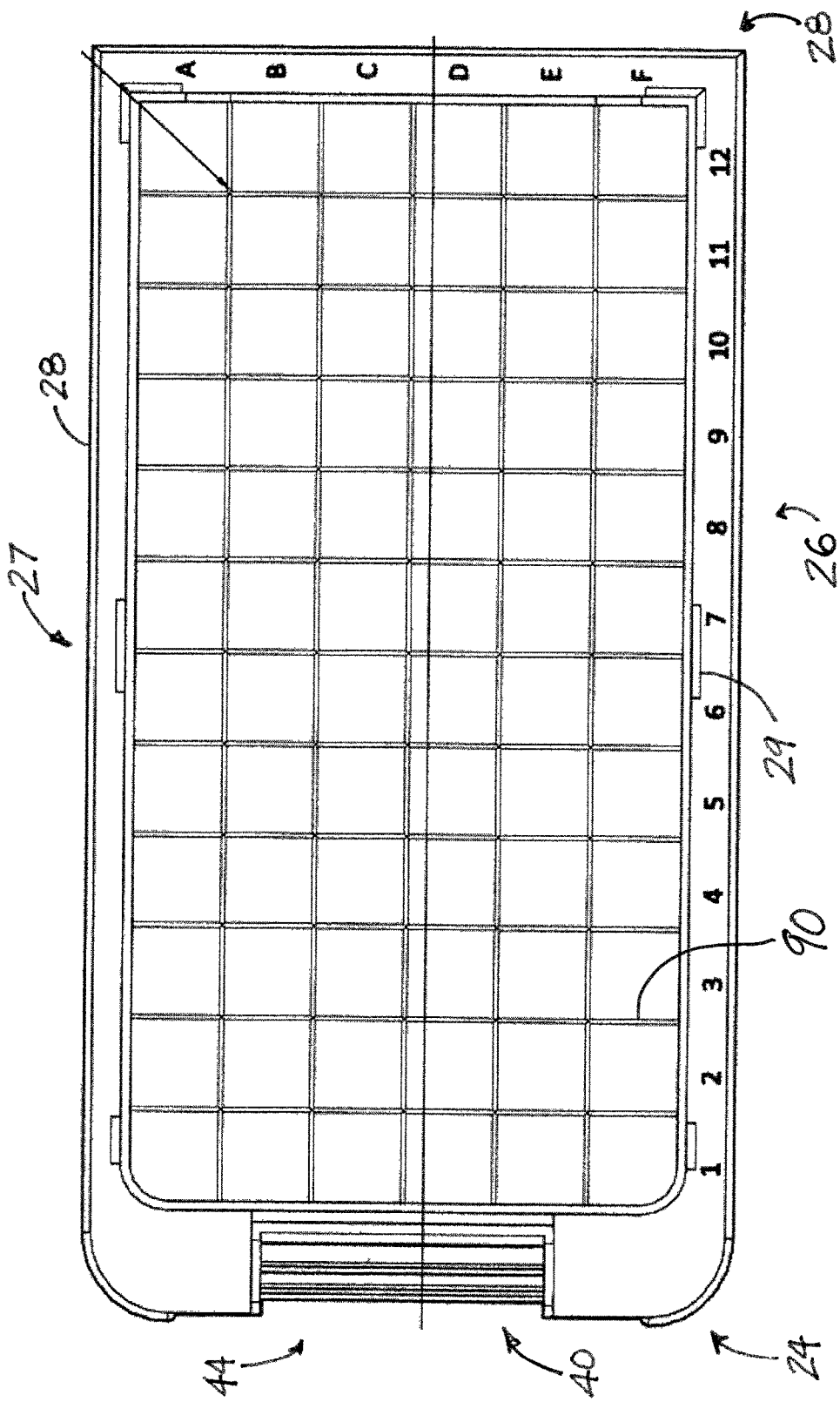
FIG. 2 is a schematic top view of the tray of the system, according to an illustrative embodiment.
Figure 3:
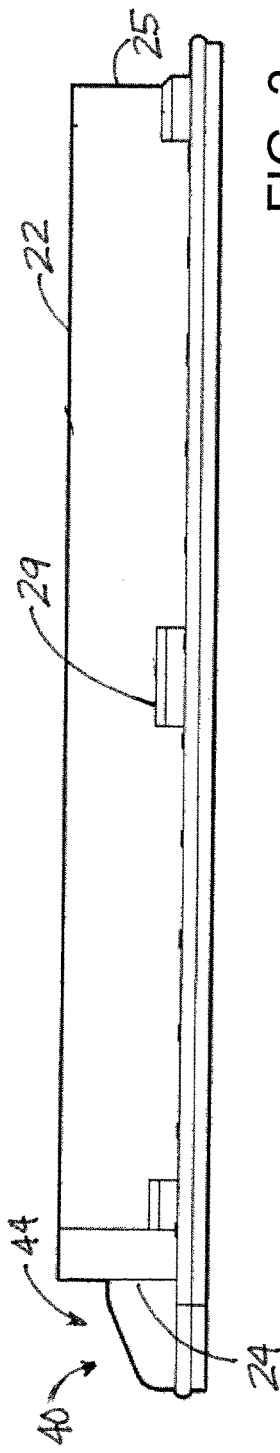
FIG. 3 is a schematic side view of the tray of the system, according to an illustrative embodiment.
Figure 4:
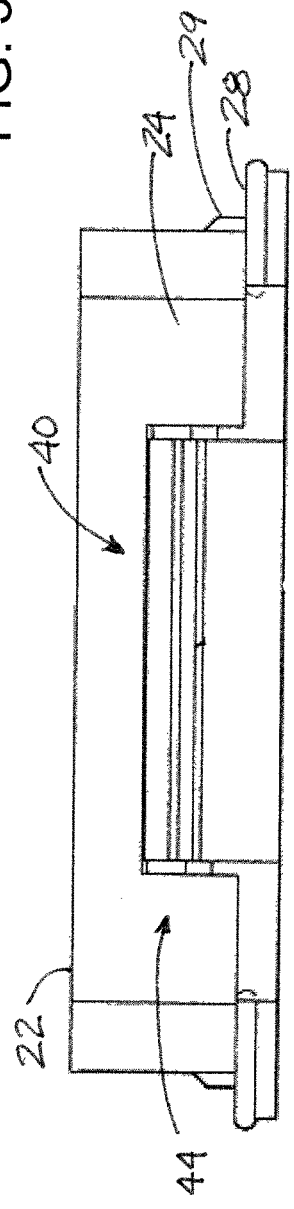
FIG. 4 is a schematic first end view of the tray of the system, according to an illustrative embodiment.
Figure 5:
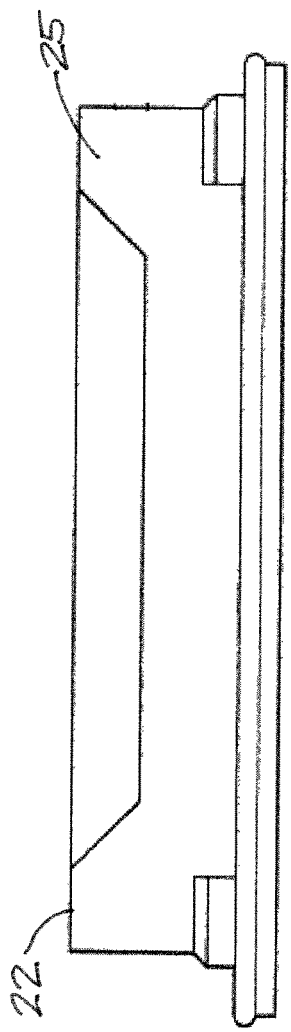
FIG. 5 is a schematic second end view of the tray of the system, according to an illustrative embodiment.
Figure 8A:
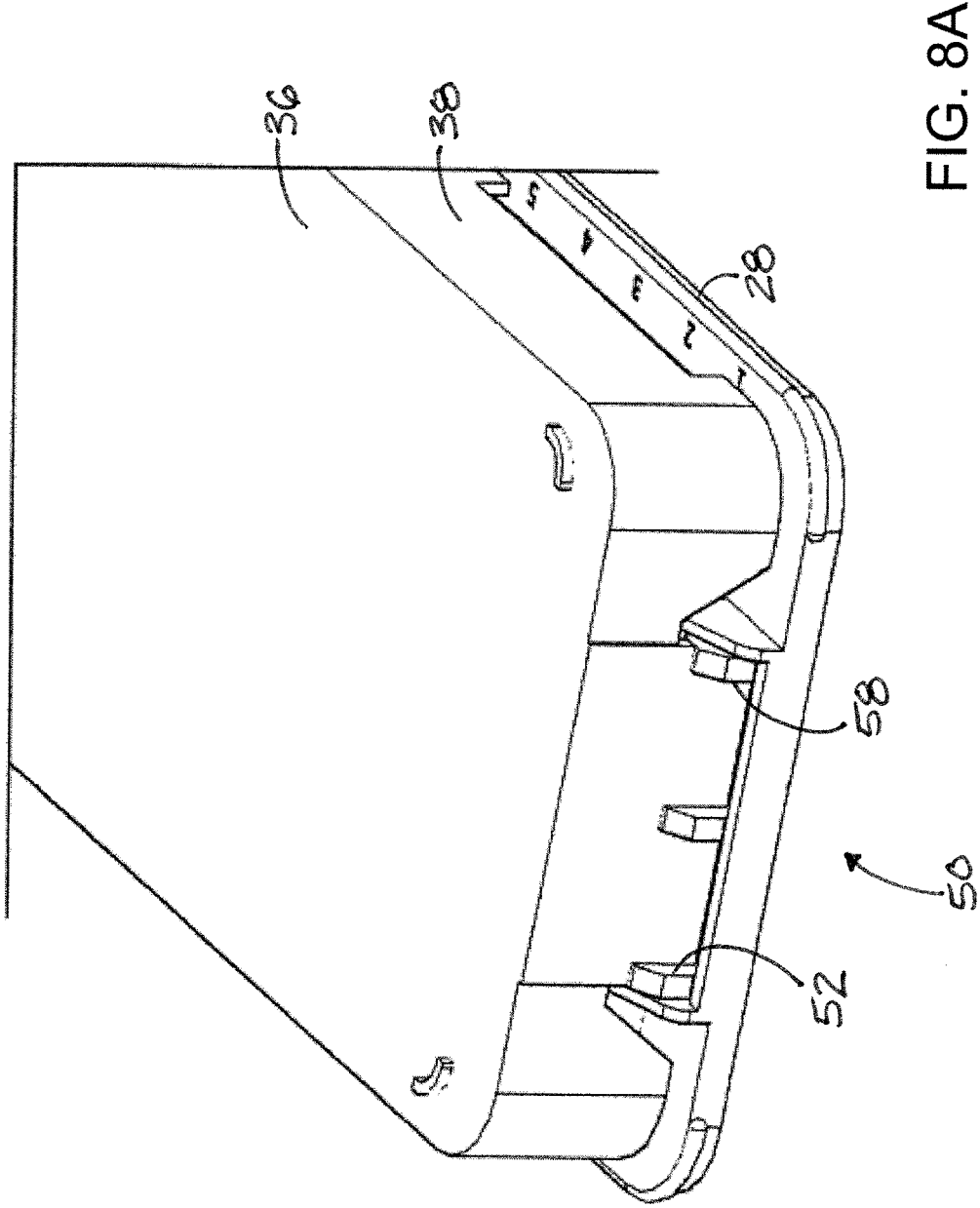
FIG. 8A is a schematic perspective end view of the cover and tray of the system in the closed condition, with one embodiment of a cover support structure, according to an illustrative embodiment.
Figure 9:
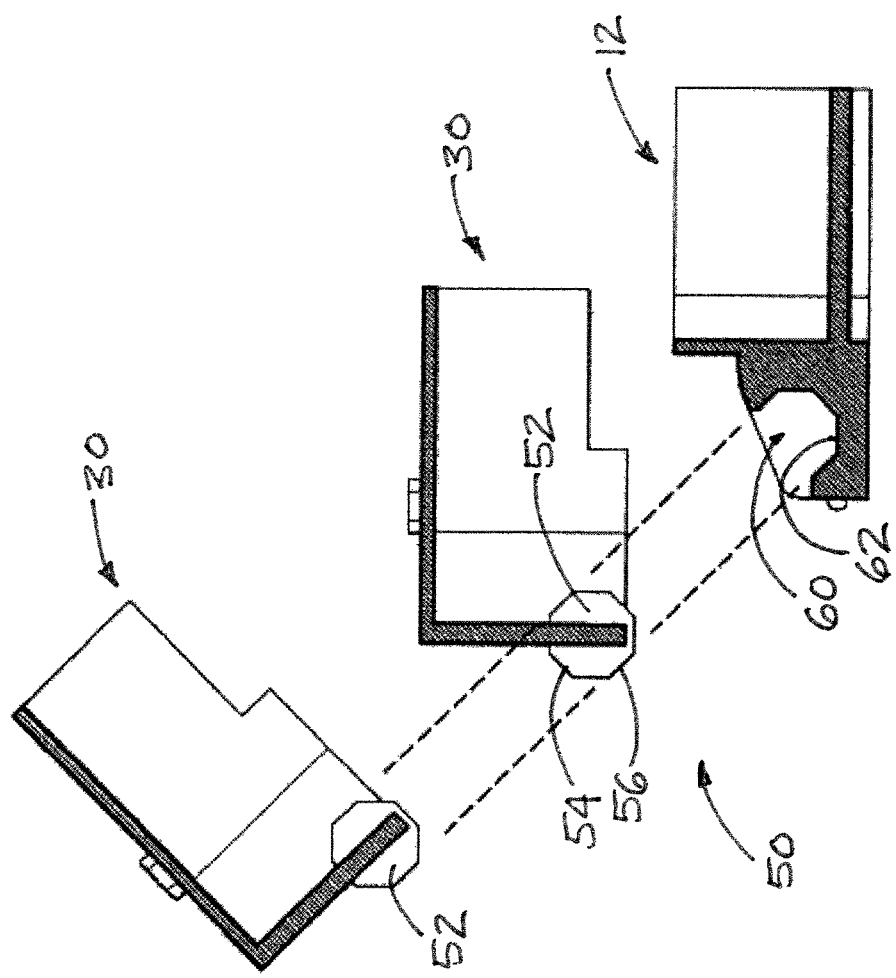
FIG. 9 is a schematic side sectional view of portions of the tray and cover in an exploded relationship with the portions of the cover shown in an orientation corresponding to the closed condition and an orientation corresponding to the access condition.
Figure 10:
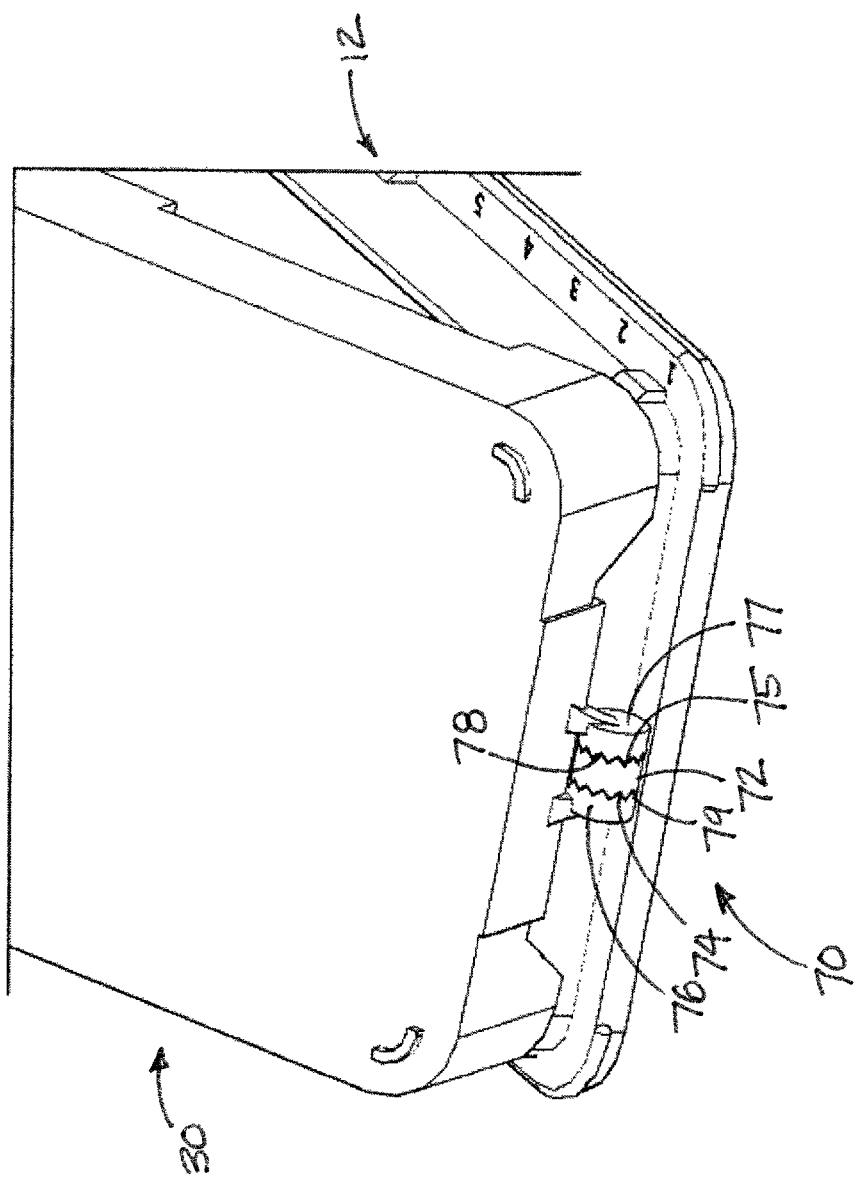
FIG. 10 is a schematic perspective end view of the system with another configuration of the cover support structure, according to an illustrative embodiment.
Figure 11:
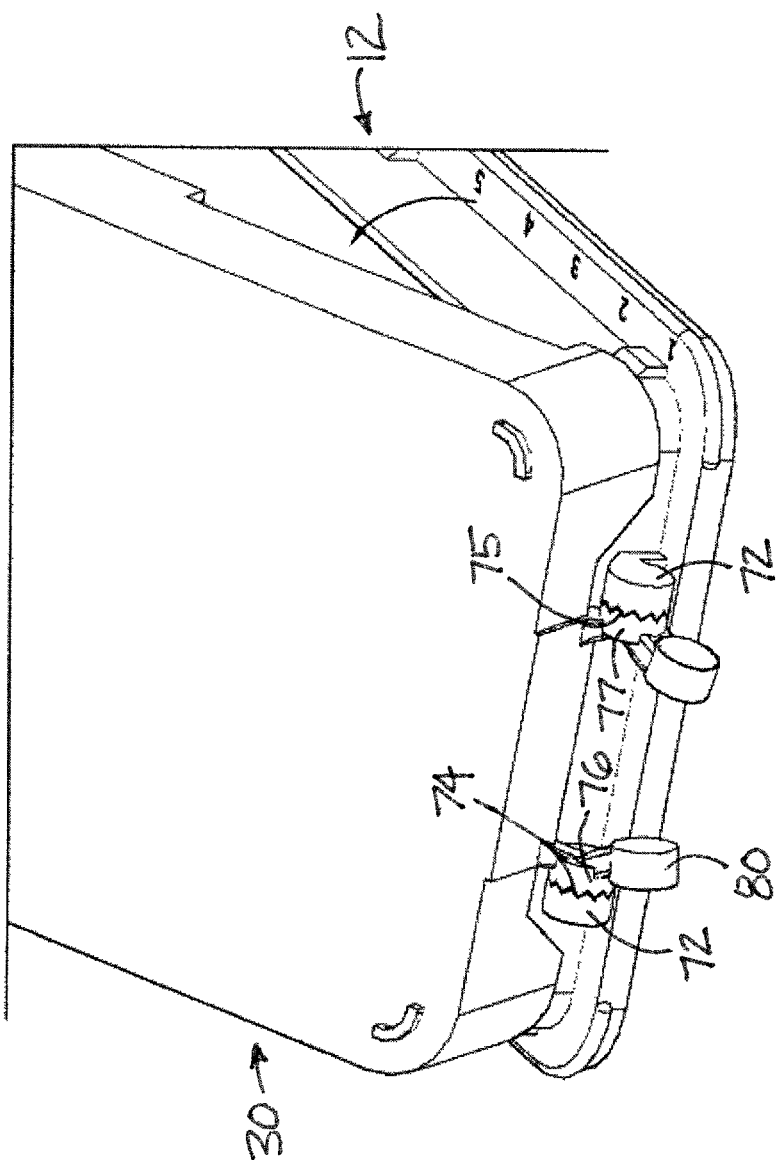
FIG. 11 is a schematic perspective end view of the system with still another configuration of the cover support structure, according to an illustrative embodiment.
Figure 12:
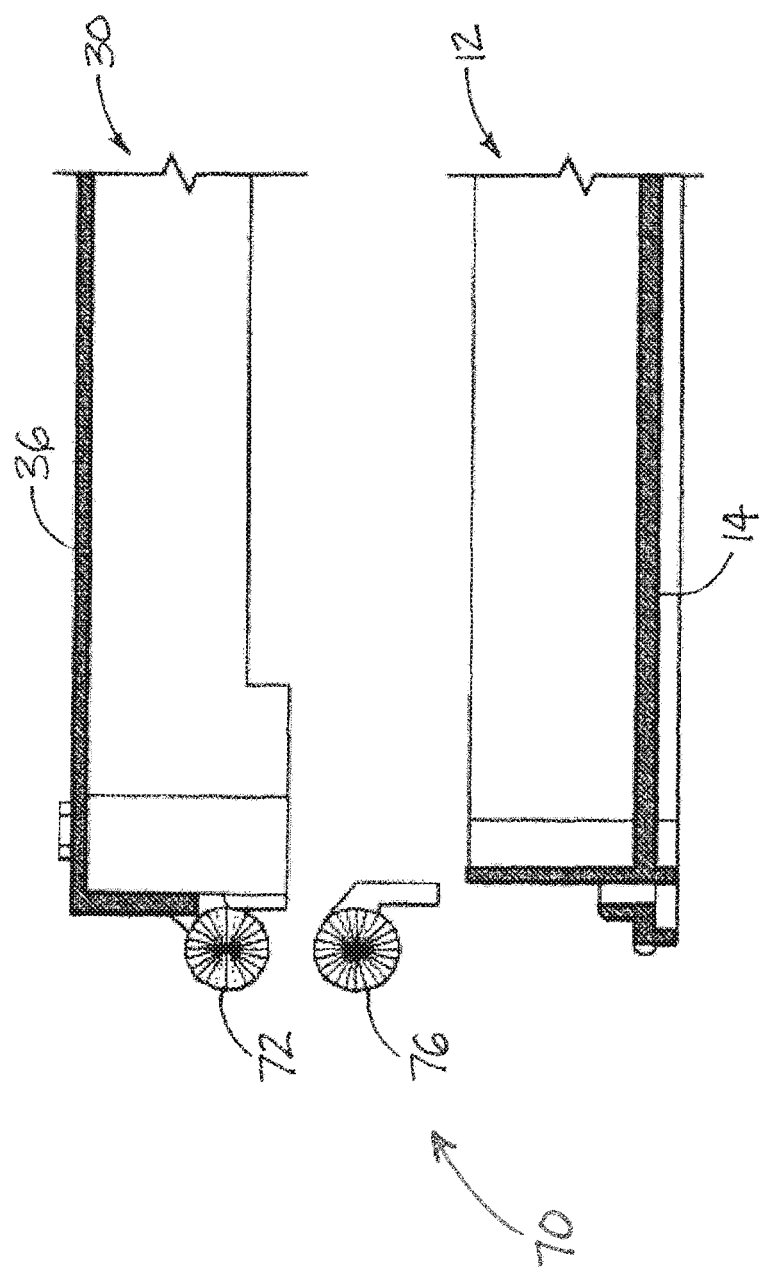
FIG. 12 is a schematic side sectional view of portions of the cover and tray of the system shown in an exploded relationship with an element of the cover support structure shown dismounted from the tray, according to an illustrative embodiment.
Figure 13:
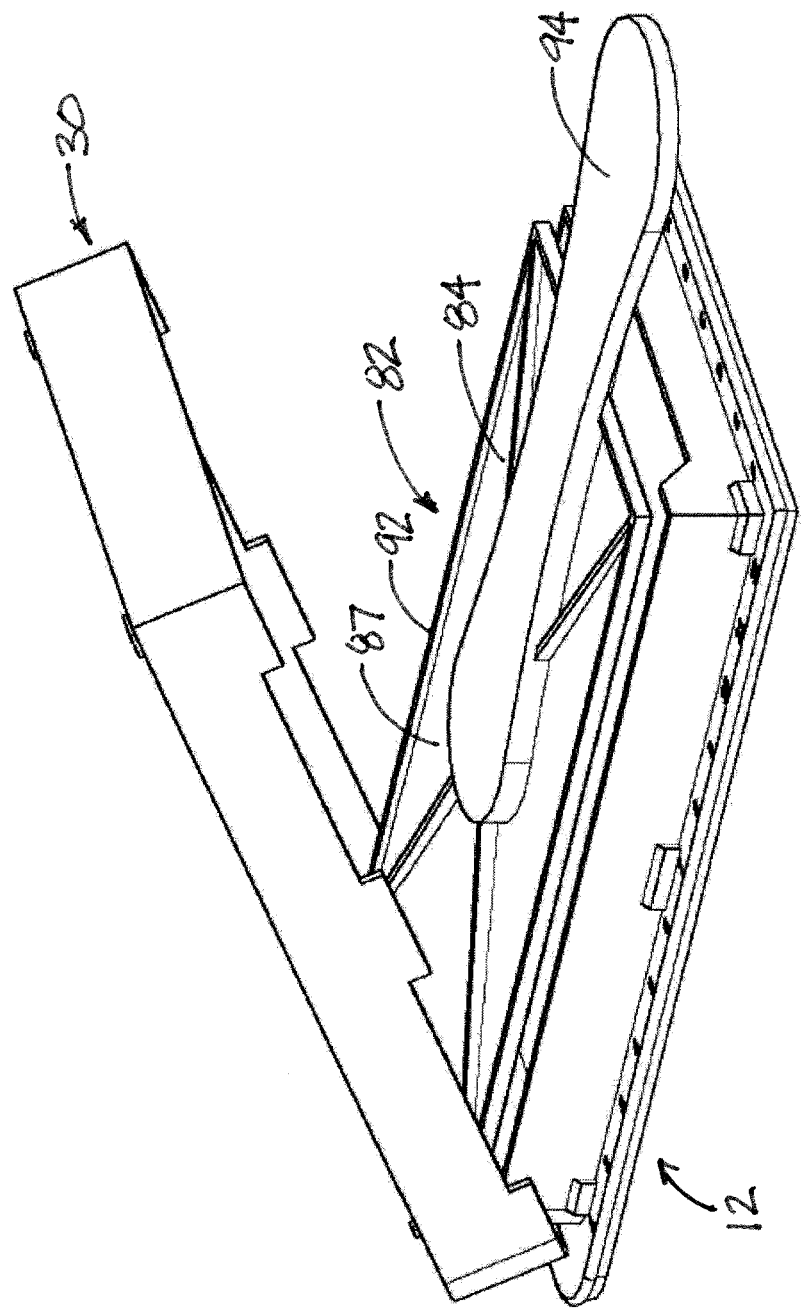
FIG. 13 is a schematic perspective view of the cover and tray and transfer tool of the system.
Figure 14:
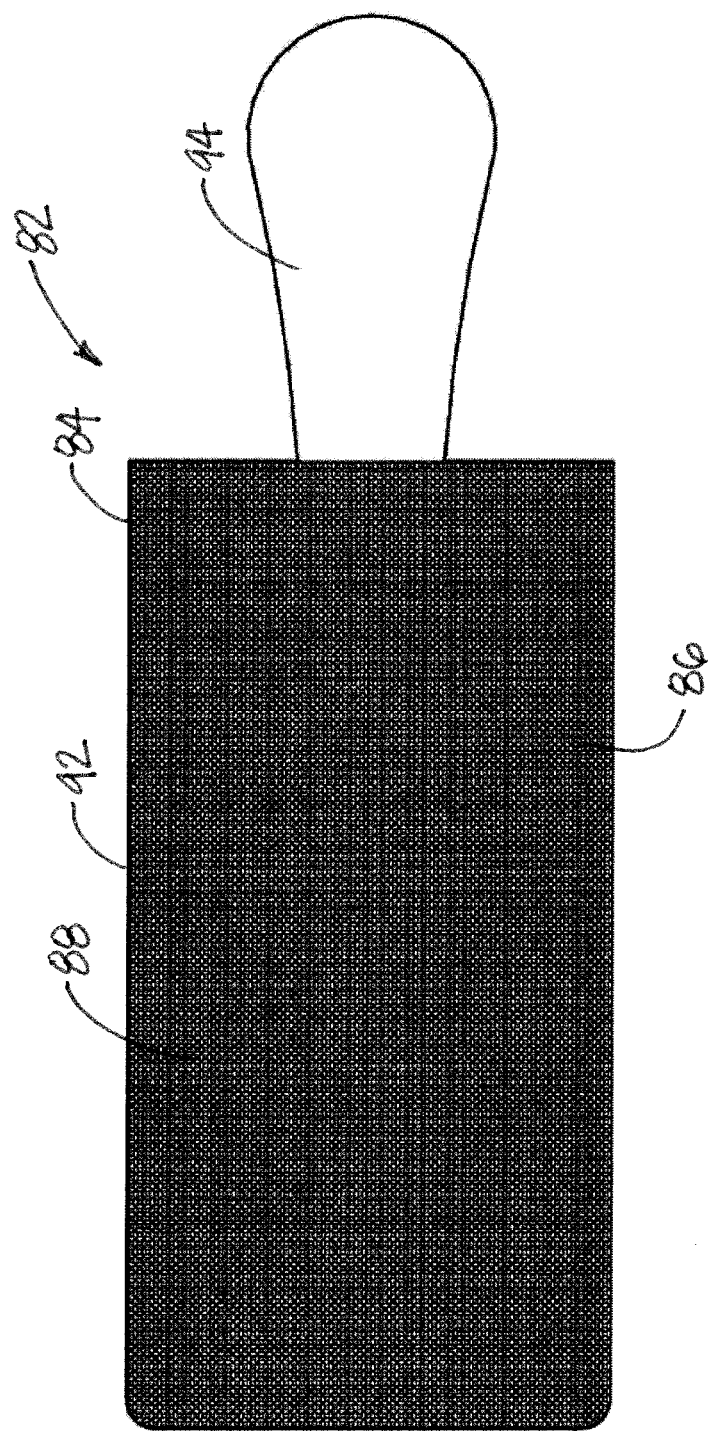
FIG. 14 is a schematic bottom view of the transfer tool of the system.

With reference now to the drawings, and in particular to FIGS. 1 through 14 thereof, a new media tray system embodying the principles and concepts of the disclosed subject matter will be described.

The applicant has recognized the inherent inconvenience and difficulty in using conventional petri dishes and covers due to the need to use two hands to move samples into or out of the media resident in the dish, one to hold the cover in proximity to the dish and another hand to hold the tool used to manipulate the sample. The applicant has devised a system which holds the cover in an access position that permits the manipulation tool to reach the sample and media while providing a large degree of protection to the sample and the media from contaminants in the environment. In one aspect, the disclosure relates to a media tray system 10 for containing media substances to promote the growth of various biological samples in an aerobic or anaerobic environment, as well as in some implementations the movement of those samples to and from the media. In general, the system may include a tray 12, a cover 30 for removably covering the tray, and a cover support structure 40 for supporting the cover in an at least one access position with respect to the tray. The system 10 may also include a transfer tool 82 for manipulating a sample or samples in the tray interior.

The tray 12 of the media tray system 10 may be configured to rest upon a surface for supporting the tray. The tray 12 may have a base wall 14 and a perimeter wall 16 which extends upwardly from the base wall to define a tray interior 18. The tray may have an upper opening 20 which is located opposite of the base wall, and the perimeter wall may have an upper edge 22 positioned opposite of the base wall to define at least a portion of the upper opening. The tray 12 may be elongated and may have a substantially rectangular shape, although other shapes may be utilized. The illustrative rectangular-shaped tray has a first end 24 and a second end 25 which is located opposite of the first end, and opposite first 26 and second 27 sides. In some embodiments, the tray may have a flange 28 which extends outwardly beyond the perimeter wall 16 and also may extend substantially in the plane of the base wall. A plurality of spacer shoulders 29 may be positioned along an outer surface of the perimeter wall. The entirety of the upper edge may lie in a common plane, but in some embodiments, the upper edge may feature a notch located toward the second end of the tray.

The cover 30 of the media tray system 10 may selectively cover or close the tray interior 18 from air and contaminants, although it is not necessarily air tight. The cover 30 may define a cover interior 32 which is in communication with the tray interior 18 when the cover is positioned on the tray. The cover may generally be substantially coextensive with the tray in order to be able to close the upper opening 20 of the tray. The cover may have a first end 34 which is positionable over the first end 24 of the tray and a second end 35 which is positionable over the second end 25 of the tray. The cover may include a top wall 36 which has a periphery 37, and a side wall 38 which extends downwardly from the top wall and is generally positioned along the periphery 37 of the top wall. The side wall 38 of the cover may be configured to extend about the perimeter wall 16 of the tray when the cover is in a closed condition with respect to the tray. The side wall 38 has a lower edge 39 which may lie substantially in a common plane, although at least one vent notch 31 may be formed into the lower edge for facilitating air movement into the interior in certain positions of the cover on the tray. Portions of the lower edge 39 may rest upon the spacer shoulders 29 of the tray when the cover is in the closed condition.

The cover support structure 40 of the system 10 may support the cover in at least one access condition in which the tray interior is accessible but the tray is not entirely uncovered. The access condition may be characterized by a gap 42 being formed between a portion of the upper edge 22 of the perimeter wall of the tray and a portion of the lower edge 39 of the side wall of the cover. The access condition may also be characterized by at least a portion of the cover being supported in a partially raised or open orientation. In some embodiments, the cover support structure 40 may be configured to support the cover in an inclined or canted orientation with respect to a plane of the base wall 14 of the tray in the access condition. In some embodiments, the cover support structure 40 may be configured to support the cover in a first access condition with a first gap having a first magnitude, as well as a second access condition with a second gap having a second magnitude, with the first and second magnitudes being different from each other and the second magnitude being greater than the first magnitude. Elements of the support structure 40 may be located on both the cover and the tray, or may be located on only the cover or the tray. The elements may be located at the first end 24 of the tray and the first end 34 of the cover, and may permit access to the tray interior 18 from a location toward the second end 25 of the tray as well as the second and 35 of the cover.

A first illustrative embodiment 44 of the cover support structure (see, e.g., FIGS. 6 and 7) may comprise a support tab 46 which may extend from the cover 30 toward the tray 12, and may extend from the side wall 38 in a generally downward direction toward the tray. The embodiment 44 may also include at least one support slot 48 which is configured to receive the support tab 46 when the cover is in the access condition. The support slot may be on the tray, such as being formed integrally with the tray. In some embodiments, a plurality of slots 48, 49 may be on the tray and may be oriented to receive the support tab in a plurality of access conditions of the cover which correspond to different gaps, such as the first gap and the second gap. In the closed condition of the cover, the support tab may be positioned in an additional slot or no slot at all.

A second illustrative embodiment 50 of the cover support structure (see e.g., FIGS. 8 and 9) may include at least one tab 52 which is formed on the cover 30 and may extend outwardly from the cover such as at the first end 34 of the cover. The tab 52 may be positioned adjacent to a section of the side wall 38 of the cover, and may be located outside of the cover interior 32. The tab 52 may have a perimeter 54 which defines a perimeter shape. In some embodiments, the perimeter shape may be polygonal, and illustratively may be octagonal. A plurality of the tabs 52, 58 may be utilized, and in some embodiments three or more tabs are used. The second illustrative embodiment 50 may also include a socket 60 which is formed on the tray 12 and which may be configured to receive the tab or tabs of the cover in the access condition, and may also receive the tab in the closed condition of the cover. The socket 60 may be configured to engage and hold the tab 52 in two or more different orientations in the access condition which may provide the first gap and the second gap. The socket 60 may have an interior shape which is generally complementary to the perimeter shape of the tab, and a plurality of surfaces 62 may define the socket and may be arranged such that the surfaces engage at least some of the perimeter edges 56 of the tab.

A third illustrative embodiment 70 of the cover support structure (see, e.g. FIGS. 10 through 12) may include a tray element 72 which is mounted on the tray 12 and has a first face 74, and may have a pair of the first faces 74, 75 which are oriented in substantially opposite directions. The third illustrative embodiment 70 may also include a cover element 76 which is mounted on the cover 30 and has a second face 78. The second face 78 may be positioned in opposition to the first face 74 of the tray element. In some embodiments a pair of the cover elements 76, 77 may be mounted on the cover and each element may have a second face which is configured so that the second faces of the cover element 76, 77 are oriented in opposition to each other and in opposition to the first faces 74, 75 of the tray element. Each of the elements 72, 76 may be inter-lockable with each other in at least the access condition of the cover, and may also be interlocked in the closed condition. Each of the elements 72, 76 may have interlocking teeth 79 which are located on the first face of the tray element and the second face of the cover element such that the interlocking teeth interlock or engage each other to thereby resist movement of the elements with respect to each other. The third embodiment 70 may also include a movement tab 80 which is mounted on at least one of the elements 72, 76 to permit application of finger pressure to the movement tab, and thereby to the respective element, to decrease the degree of interlock of the teeth of the elements together to facilitate movement of the cover with respect to the tray.

The transfer tool 82 of the system 10 may be configured to removably insert into the tray interior for transferring samples into and out of the tray interior 18, such as onto and off of the surface of media contained within the tray interior. The transfer tool 82 may include a contact portion 84 which is configured to contact a surface in the tray interior, such as the upper surface of the media. The contact portion 84 may have a front 86 and a back 87, and the front of the contact portion may have a contact face 88. The contact face 88 may be substantially planar, and may have a grid 90 marked thereon for determining positions of various colonies of organisms on the media as well as on the contact face. The contact portion 84 has a perimeter 92 which may have a size and shape which is configured to pass between the perimeter wall 16 of the tray such that the contact portion may be easily inserted into the tray interior. The transfer tool 82 may also include a handle portion 94 which extends from the contact portion 84 and is configured to extend from the tray interior when the contact portion is positioned in the tray interior. The handle portion 94 may be elongated and extend in a direction substantially parallel to the plane of the contact face to thereby minimize the dimension of the profile of the tool 82 along an axis perpendicular to the plane of the contact face to thereby facilitate movement of the tool into and out of the tray interior. The handle portion 94 may extend from the back 87 of the contact portion into and out of the tray interior vertical program profile It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

I claim:

1. A media tray system comprising:
    a tray having a base wall and a perimeter wall extending upwardly from the base wall to define a tray interior, the perimeter wall having an upper edge opposite of the base wall and defining at least a portion of an upper opening of the tray;
    a cover having a top wall and a side wall extending downwardly from the top wall to extend about the perimeter wall of the tray when the cover is in a closed condition with respect to the tray, the side wall having a lower edge; and
    a cover support structure located at the first end of the tray and the first end of the first end of the cover,
    wherein the cover support structure is configured to support the cover in an access condition permitting access to the tray interior of the tray through a gap formed between an upper edge of the tray and the lower edge of the cover; and
    wherein the access condition comprises at least two orientations of the cover with respect to the tray, and wherein a magnitude of the gap between the upper edge of the tray and lower edge of the cover is different for each of the at least two orientations.

2. The system of claim 1 wherein the access condition is characterized by at least a portion of the cover being supported in a partially raised orientation of the at least two orientations.

3. The system of claim 1 wherein the access condition is characterized by at least a portion of the cover being supported in a partially open orientation of the at least two orientations.

4. The system of claim 1 wherein the cover support structure is configured to support the cover in an inclined orientation of the at least two orientations with respect to the tray in the access condition to provide the gap.

5. The system of claim 1 wherein the cover support is configured to support the cover in a first access condition in which the gap has a first gap magnitude and a second access condition in which the gap has a second gap magnitude, the first gap magnitude and the second gap magnitude being different.

6. The system of claim 1 wherein the tray has a first end and a second end located opposite of the first end, the cover having a first end of the cover having positionable over the first end of the tray and a second end of the cover being positionable over the second end of the tray, and the cover support structure is located at the first end of the tray and the first end of the first end of the cover to form the gap at the second ends of the tray and the cover.

7. The system of claim 1 additionally comprising a transfer tool configured to removably insert into the tray interior of the tray for transferring substances into and out of the tray interior.

8. The system of claim 7 wherein the transfer tool includes a contact portion configured to contact surfaces in the tray interior, the contact portion having a front and a back, and a handle portion extending from the contact portion and being configured to extend from the tray interior when the contact portion is positioned in the tray interior.

9. The system of claim 8 wherein the transfer tool includes a handle portion extending from the contact portion and being configured to extend from the tray interior when the contact portion is positioned in the tray interior.

10. The system of claim 8 wherein the contact portion has a perimeter with a size and shape configured to position edges of the contact portion adjacent to all inner surfaces of the perimeter wall of the tray when the contact portion is positioned in the tray interior.

11. The system of claim 8 wherein the contact portion has a contact face on the front; and wherein the contact face has a grid thereon.

12. The system of claim 8 wherein the perimeter wall comprises a plurality of wall portions, the plurality of wall portions including a pair of substantially parallel spaced end wall portions located at ends of the tray and a pair of substantially parallel spaced side wall portions; and wherein the contact portion has a perimeter edge with opposite end edge portions and opposite side edge portions, the perimeter edge having a size and shape configured to position the end edge portions of the perimeter edge at the end wall portions of the perimeter wall and to position the side edge portions of the perimeter edge at the side wall portions of the perimeter wall.

13. The system of claim 12 wherein the side wall portions each have inner surfaces which intersect an inner surface of a first one of the end wall portions in perpendicular orientations and the inner surfaces of the side wall portions each intersect an inner surface of a second one of the end wall portions in arcuate orientations; and wherein the contact portion of the transfer tool has a perimeter edge with opposite end edge portions and opposite side edge portions, the side edge portions each intersecting a first one of the end edge portions in a perpendicular relationship and the side edge portions intersecting a second one of the end edge portions in arcuate relationship such that the contact portion of the transfer tool is only able to be inserted into the tray interior in a single end to end orientation.

14. The system of claim 1 wherein the cover support structure comprises a support tab extending from the cover toward the tray; and at least one support slot on the tray and configured to receive the support tab when the cover is in the access condition.

15. The system of claim 14 wherein the at least one support slot comprises a plurality of slots oriented to receive the support tab in each of the plurality of orientations of the access condition having gaps of different magnitudes.

16. The system of claim 1 wherein the access condition comprises at least three orientations of the cover with respect to the tray with each of the at least three orientations producing a different magnitude of the gap between the upper edge of the tray and lower edge of the cover.

17. The system of claim 1 wherein the perimeter wall comprises a plurality of wall portions, the plurality of wall portions including a pair of substantially parallel spaced end wall portions located at ends of the tray and a pair of substantially parallel spaced side wall portions, the cover support structure being positioned adjacent to a first one of said the end wall portions; and wherein a section of the upper edge of the perimeter wall on a second one of the end wall portions defines a notch such that the section of the upper edge is closer to the base wall than sections of the upper edge of the perimeter wall on the first end wall portion and the pair of side wall portions to accommodate insertion of a portion of a tool into the tray interior.

18. The system of claim 1 wherein the perimeter wall comprises a plurality of wall portions, the plurality of wall portions including a pair of substantially parallel spaced end wall portions located at ends of the tray and a pair of substantially parallel spaced side wall portions; and wherein the base has an inner surface defining a bottom of the tray interior, the inner surface of the base extending without interruption between the end wall portions and between the side wall portions such that the tray defines a single tray interior within the perimeter wall.

19. The system of claim 1 wherein the cover support structure comprises:

at least one tab formed on the cover and extending downwardly from the cover, the tab having a perimeter with a perimeter shape formed by a plurality of perimeter edges defining the shape; and a socket formed on the tray and configured to receive the at least one tab of the cover to support the cover in at least the access condition, a plurality of surfaces defining the socket and being arranged to engage at least some of the perimeter edges of the tab.

20. The system of claim 19 wherein the socket is configured to engage and hold the tab in a plurality of orientations of the access condition having gaps of different magnitudes.

21. The system of claim 1 wherein the cover support structure comprises:

a tray element mounted on the tray having a first face and a cover element mounted on the cover and having a second face, the second face of the cover element being positioned in opposition to the first face of the tray element, each of the elements being interlockable with each other in at least the access condition of the over.

22. The system of claim 21 wherein each of the elements having interlocking teeth, the interlocking teeth being located on the first face of the tray element and the second face of the cover element.

23. The system of claim 21 wherein the tray element has a pair of first faces oriented in substantially opposite directions; and a pair of the cover elements are mounted on the cover, each of the cover elements having a second face configured such that the second faces are oriented in opposition to each other and engage the first faces of the tray element.

* * * * *